(12) United States Patent
Luhta et al.

(10) Patent No.: US 7,873,144 B2
(45) Date of Patent: Jan. 18, 2011

(54) PULSED X-RAY FOR CONTINUOUS DETECTOR CORRECTION

(75) Inventors: Randall P. Luhta, Highland Heights, OH (US); Marc A. Chappo, Elyria, OH (US); Brian E. Harwood, Wickliffe, OH (US); Rodney A. Mattson, Mentor, OH (US); Chris J. Vrettos, Willoughby, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 543 days.

(21) Appl. No.: 11/721,163

(22) PCT Filed: Dec. 5, 2005

(86) PCT No.: PCT/IB2005/054069

§ 371 (c)(1),
(2), (4) Date: Jun. 8, 2007

(87) PCT Pub. No.: WO2006/064403

PCT Pub. Date: Jun. 22, 2006

(65) Prior Publication Data

US 2009/0238330 A1 Sep. 24, 2009

Related U.S. Application Data

(60) Provisional application No. 60/637,476, filed on Dec. 17, 2004.

(51) Int. Cl.
*H05G 1/64* (2006.01)

(52) U.S. Cl. .................. 378/98.8; 378/98.11; 378/207; 250/252.1; 250/369; 250/370.09; 250/370.11

(58) Field of Classification Search .................. 378/19, 378/98.8, 98.11, 207; 250/369, 370.09, 370.11, 250/252.1
See application file for complete search history.

(56) References Cited

U.S. PATENT DOCUMENTS 4,068,306 A 1/1978 Chen et al.
(Continued)

FOREIGN PATENT DOCUMENTS

DE 4303948 A1 8/1994
(Continued)

OTHER PUBLICATIONS

Overdick et al., Temporal Artefacts in Flat Dynamic X-ray Detectors, 2002, SPIE, vol. 4320, pp. 47-58.*
(Continued)

*Primary Examiner*—Edward J Glick
*Assistant Examiner*—John M Corbett (57) ABSTRACT

A radiographic imaging apparatus (10) comprises a primary radiation source (14) which projects a beam of radiation into an examination region (16). A detector (18) converts detected radiation passing through the examination region (16) into electrical detector signals representative of the detected radiation. The detector (18) has at least one temporally changing characteristic such as an offset B(t) or gain A(t). A grid pulse means (64) turns the primary radiation source (14) ON and OFF at a rate between 1000 and 5000 pulses per second, such that at least the offset B(t) is re-measured between 1000 and 5000 times per second and corrected a plurality of times during generation of the detector signals. The gain A(t) is measured by pulsing a second pulsed source (86, 100, 138) of a constant intensity (XRef) with a second pulse means (88). The gain A(t) is re-measured and corrected a plurality of times per second during generation of the detector signals.

25 Claims, 9 Drawing Sheets

U.S. PATENT DOCUMENTS

| | | | |
|---|---|---|---|
| 4,341,956 A | | 7/1982 | Bax |
| 5,012,498 A | | 4/1991 | Cuzin et al. |
| 5,220,589 A | | 6/1993 | Gard |
| 5,379,333 A | * | 1/1995 | Toth .......................... 378/16 |
| 5,430,785 A | * | 7/1995 | Pfoh et al. .................. 378/19 |
| 5,734,691 A | | 3/1998 | Hu et al. |
| 5,923,722 A | * | 7/1999 | Schulz ....................... 378/98.8 |
| 6,373,920 B1 | * | 4/2002 | Hsieh ......................... 378/98.11 |
| 6,418,185 B1 | | 7/2002 | Besson et al. |
| 6,457,861 B1 | | 10/2002 | Petrick et al. |
| 6,529,575 B1 | * | 3/2003 | Hsieh .......................... 378/4 |
| 2002/0024017 A1 | * | 2/2002 | Overdick et al. ....... 250/370.11 |
| 2003/0007601 A1 | * | 1/2003 | Jaffray et al. ................ 378/65 |
| 2004/0022352 A1 | * | 2/2004 | Suzuki ........................ 378/19 |

FOREIGN PATENT DOCUMENTS

DE            19631624 C1 * 10/1997

OTHER PUBLICATIONS

Wischmann et al., Correction of Amplifier Non-Linearity, Offset, Gain, Temporal Artifacts, and Defects for Flat Panel Digital Imaging Devices, 2002, SPIE, vol. 4682, pp. 427-437.*

Zhao et al., Investigation of lag and ghosting in amorphous selenium flat-panel detectors, 2002, SPIE, vol. 4682, pp. 9-20.*

Elbakri, Statistical Reconstruction Algorithms for Polyenergetic X-ray Computed Tomography, 2003, Doctoral Dissertation, University of Michigan, 175 pages.*

Tang, X-ray Flat Panel Imager Based Cone Beam Volume Computed Tomography, 2001, Doctoral Dissertation, University of Rochester.*

Siewerdsen et al., A ghost story: Spatio-temporal response characteristics of an indirect-detection flat-panel imager, 1999, Medical Physics, vol. 26, No. 8, pp. 1624-1641.*

Chabbal et al., Amorphous Silicon X-ray Image Sensor, 1996, SPIE vol. 2708, pp. 499-510.*

* cited by examiner

PULSED X-RAY FOR CONTINUOUS DETECTOR CORRECTION

CROSS REFERENCE TO RELATED APPLICATIONS

This application claims the benefit of U.S. provisional application Ser. No. 60/637,476 filed Dec. 17, 2004, which is incorporated herein by reference.

The present application relates to the diagnostic imaging arts. It finds particular application in the computed tomography imaging, and will be described with particular reference thereto. However, it also finds application in other imaging apparatuses and methods that employ x-ray detectors.

CT scanners typically include an x-ray source and arrays of x-ray detectors secured respectively on diametrically opposite sides of a gantry. During a scan of a patient located within the bore of the gantry, the gantry rotates about a rotation axis while an x-ray source emits x-rays during the data collection period of the scan. The x-rays are collected by the detector which includes a plurality of detector elements.

Typically, the x-ray detector used in a CT scanner includes a layer of scintillating crystals which is coupled to an array of silicon photodiodes. The scintillating crystals absorb x-rays that have passed through the patient and produce light in proportion to the intensity of the absorbed x-rays. The photodiodes absorb the light produced by the scintillating crystals and convert it into an electrical current in proportion to the light absorbed. The ideal detector produces a signal current $S(t)$ in direct proportion to the x-ray intensity $X$ incident to the detector.

Generally, x-ray detectors are characterized by a time dependent gain $A(t)$ and offset $B(t)$. Offset is represented by a residual signal which stays ON after the x-ray source is turned OFF. Typically, the scintillating layer of x-ray detector is selected from the materials which have the gain $A(t)$ and offset $B(t)$ nearly constant with time. Most often, for such a detector (with nearly constant gain $A(t)$ and offset $B(t)$), no correction for changes in gain and/or offset during a scan are made. In some scanning systems, only a minor correction for changes in offset $B(t)$ is made during a scan. Usually, the offset $B(t)$ of the detector is calibrated once every scan, e.g. approximately every 30 seconds. The gain $A(t)$ of the detector may be calibrated once every month. Therefore, the materials for the detectors are carefully selected such that the changes in offset and gain are so minor between calibrations than can be neglected.

Scintillating crystal materials, for which gain and offset are nearly constant, are expensive which adds a substantial cost to the cost of the detector. However, if the lower grade, lower cost scintillating crystal materials are used in a CT scanner, the changes in gain $A(t)$ and offset $B(t)$ during a scan may be substantial and cannot be neglected.

Another problem encountered in the modern CT scanners is the reduction in signal per detector as the detectors are made smaller with correspondingly thinner slices. The reduction in signal per detector can cause artifacts in CT scans where high attenuation of the patient results in low signal conditions, e.g. when the patient is imaged through the shoulders. The low signal condition can be overcome by using a detector with a higher gain $A(t)_x$, thus improving the signal-to-noise ratio.

The materials with a high gain are known. Such materials could have been used in the CT detector, if it were not for the known problem of the change in offset and/or gain. For example, the direct conversion semiconductors (x-ray photoconductors), such as CdZnTe, CdTe, TlBr, PbO and the like, can provide a gain as much as ten times greater than the scintillator-photodiode detectors. The higher gain could improve imaging in the scanners with thinner slices. However, the gain and offset of the photoconductors are not stable and vary substantially with time.

The present invention contemplates an improved apparatus and method that overcomes the aforementioned limitations and others.

According to one aspect of the present application, a radiographic imaging apparatus is disclosed. A primary radiation source projects a beam of radiation into an examination region in which a subject is disposed for an examination. A detector converts detected radiation passing through the examination region into electrical detector signals representative of the detected radiation and at least one temporally changing characteristic. A correction means determines a correction to the detector signals to compensate for the at least one temporally changing characteristic a plurality of times during generation of the detector signals and corrects the detector signals with the determined corrections.

According to another aspect, a radiographic imaging method is disclosed. A beam of radiation is projected into an examination region in which a subject is disposed for an examination. Detected radiation passing through the examination region is converted into electrical detector signals representative of the detected radiation and at least one temporally changing characteristic. A correction to the detector signals is determined to compensate for the at least one temporally changing characteristic a plurality of times during generation of the detector signals. The detector signals are corrected with the determined corrections.

One advantage of the present application resides in continuously correcting the gain and offset of an x-ray detector during the CT scan.

Another advantage resides in utilizing existing imaging detectors.

Another advantage resides in utilizing existing conversion electronics.

Another advantage resides in not adding time to the scan.

Another advantage resides in effectively preventing artifacts in the image due to a change in offset and/or gain of detector during one scan.

Another advantage resides in utilizing lower cost detector materials which are known to have time varying characteristics.

Another advantage resides in reducing a thickness of the scanner slice by using x-ray photoconductors.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 1:
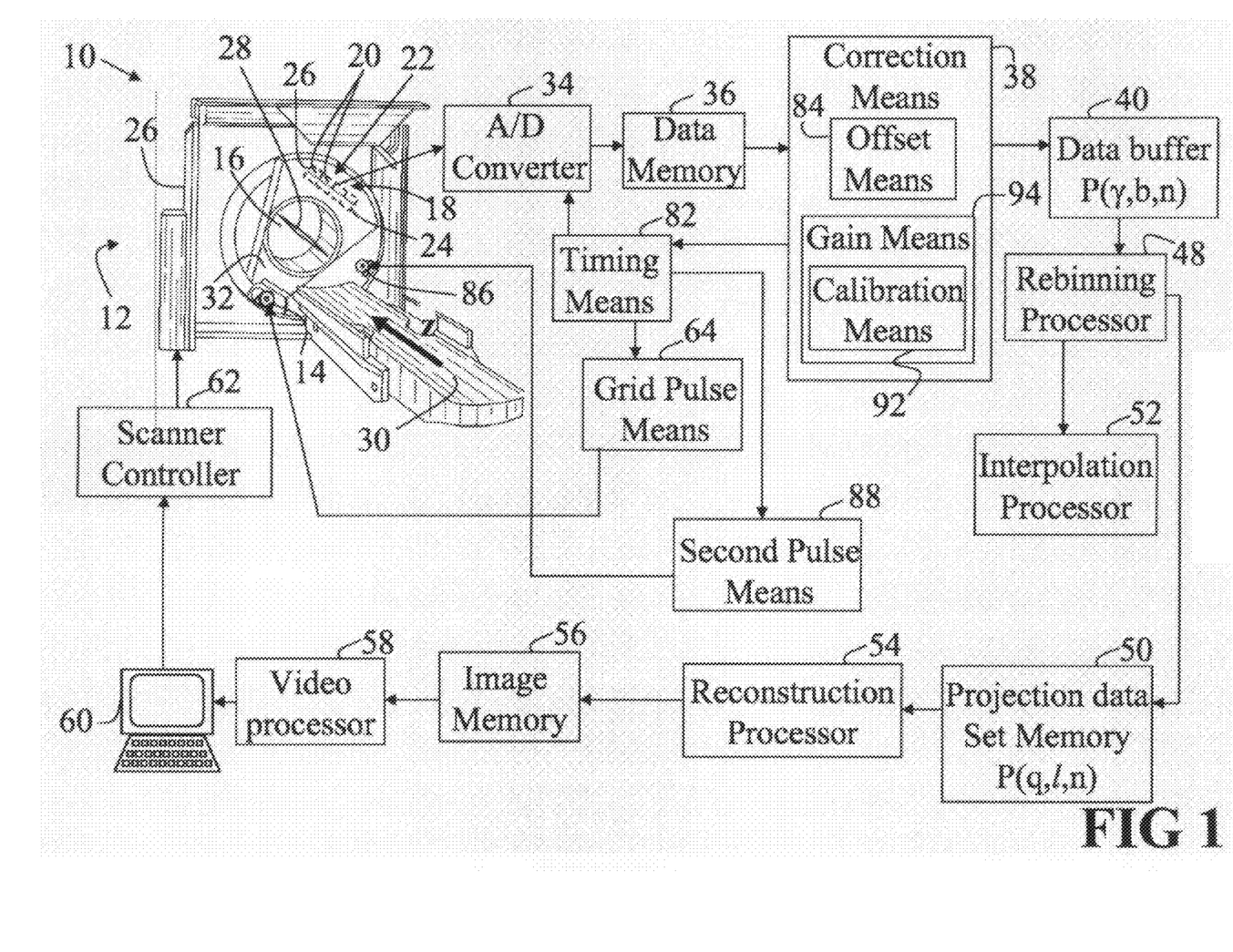
FIG. 1 shows a diagrammatic representation of a computed tomography imaging system.

With reference to FIG. 1, an imaging system 10 includes a computed tomography scanner 12 which houses or supports a primary radiation source 14, which in one embodiment, is an x-ray source or x-ray tube, that projects a radiation beam into an examination region 16 defined by the scanner 12. After passing through the examination region 16, the radiation beam is detected by a two-dimensional radiation detector 18 which includes a plurality of detection modules or detection elements 20 arranged to detect the radiation beam after passing through the examination region 16. The detector 18 includes an x-ray to analog signal converting layer 22 which has a gain A(t) and/or offset B(t) characteristics that typically change with time. In one embodiment, the converting layer 22 includes an array of scintillating crystals or a scintillator or a scintillating layer 24 which is coupled with an array of photodiodes 26. In another embodiment, the converting layer 22 includes a plurality of direct conversion semiconductors or x-ray photoconductors such as CZT, CdTe, TlBr, PbO and the like. Typically, the x-ray tube 14 produces a diverging x-ray beam having a cone beam, wedge beam, or other beam geometry that expands as it passes through the examination region 16 to substantially fill the area of the radiation detector 18.

An imaging subject 28 (shown in the examination region 16) is placed on a couch 30 or other support that moves the imaging subject into the examination region 16. The couch 30 is linearly movable along an axial direction $O_Z$ (designated as a Z-direction in FIG. 1.) The radiation source 14 and the radiation detector 18 are oppositely mounted with respect to the examination region 16 on a rotating gantry 32, such that rotation of the gantry 32 effects revolving of the radiation source 14 about the examination region 16 to provide an angular range of views. The acquired data is referred to as projection data since each detector element detects a signal corresponding to an attenuation line integral taken along a line, narrow cone, or other substantially linear projection extending from the source to the detector element.

In one embodiment, an axial projection data set is acquired with the rotating gantry 32 rotating while the couch 30 is stationary. The axial projection data set includes a plurality of axial slices corresponding to rows or columns of detector elements transverse to the axial or Z-direction. Optionally, additional axial slices are acquired by performing repeated axial scans and moving the couch 30 between each axial scan.

In another embodiment, a helical projection data set is acquired by rotating the gantry 32 simultaneously with continuous linear motion of the couch 30 to produce a helical trajectory of the radiation source 14 around the imaging subject disposed on the couch 30.

During scanning, some portion of the radiation passing along each projection is absorbed by the imaging subject to produce a generally spatially varying attenuation of the radiation. The detection elements 20 of the detector 18 sample the radiation intensities across the radiation beam to generate radiation absorption projection data. An analog to digital converter 34 converts the analog signal collected by the detector 18 into a series of digital numbers. The digital data including both x-ray attenuation measurements of the subject, offset measurements, and gain measurements is stored in a data memory 36. A correction means 38 applies a mathematical correction to the projection data to correct for changes in the detector offset B(t) and/or gain A(t) which vary with time, as will be discussed in a greater detail below. In one embodiment, the correction means 38 is incorporated with the analog to digital converter 34. The corrected projection data is stored in a buffer memory 40.

For a source-focused acquisition geometry in a multi-slice scanner, readings of the attenuation line integrals or projections of the projection data set stored in the buffer memory 40 can be parameterized as $P(\gamma,\beta,n)$, where $\gamma$ is the source angle of the radiation source 14 determined by the position of the rotating gantry 32, $\beta$ is the angle within the fan ($\beta \epsilon [-\Phi/2, \Phi/2]$, where $\Phi$ is the fan angle), and n is the detector row number in the $O_Z$ direction. In one embodiment, a rebinning processor 48 rebins the projection data into a parallel, non-equidistant raster of canonic trans-axial coordinates. The rebinning can be expressed as $P(\gamma,\beta,n) \rightarrow P(\theta,l,n)$, where $\theta$ parameterizes the projection number that is composed of parallel readings parameterized by l which specifies the distance between a reading and the isocenter, and n is the detector row number in the $O_Z$ direction.

The rebinned parallel ray projection data set $P(\theta,l,n)$ is stored in a projection data set memory 50. Optionally, the projection data is interpolated by a interpolation processor 52 into equidistant coordinates or into other desired coordinates spacings before storing the projection data $P(\theta,l,n)$ in the projection data set memory 50. A reconstruction processor 54 applies filtered backprojection or another image reconstruction technique to reconstruct the projection data set into one or more reconstructed images that are stored in a reconstructed image memory 56. The reconstructed images are processed by a video processor 58 and displayed on a user interface 60 or is otherwise processed or utilized. In one embodiment, the user interface 60 also enables a radiologist, technician, or other operator to interface with a computed tomography scanner controller 62 to implement a selected axial, helical, or other computed tomography imaging session.

Figure 2:
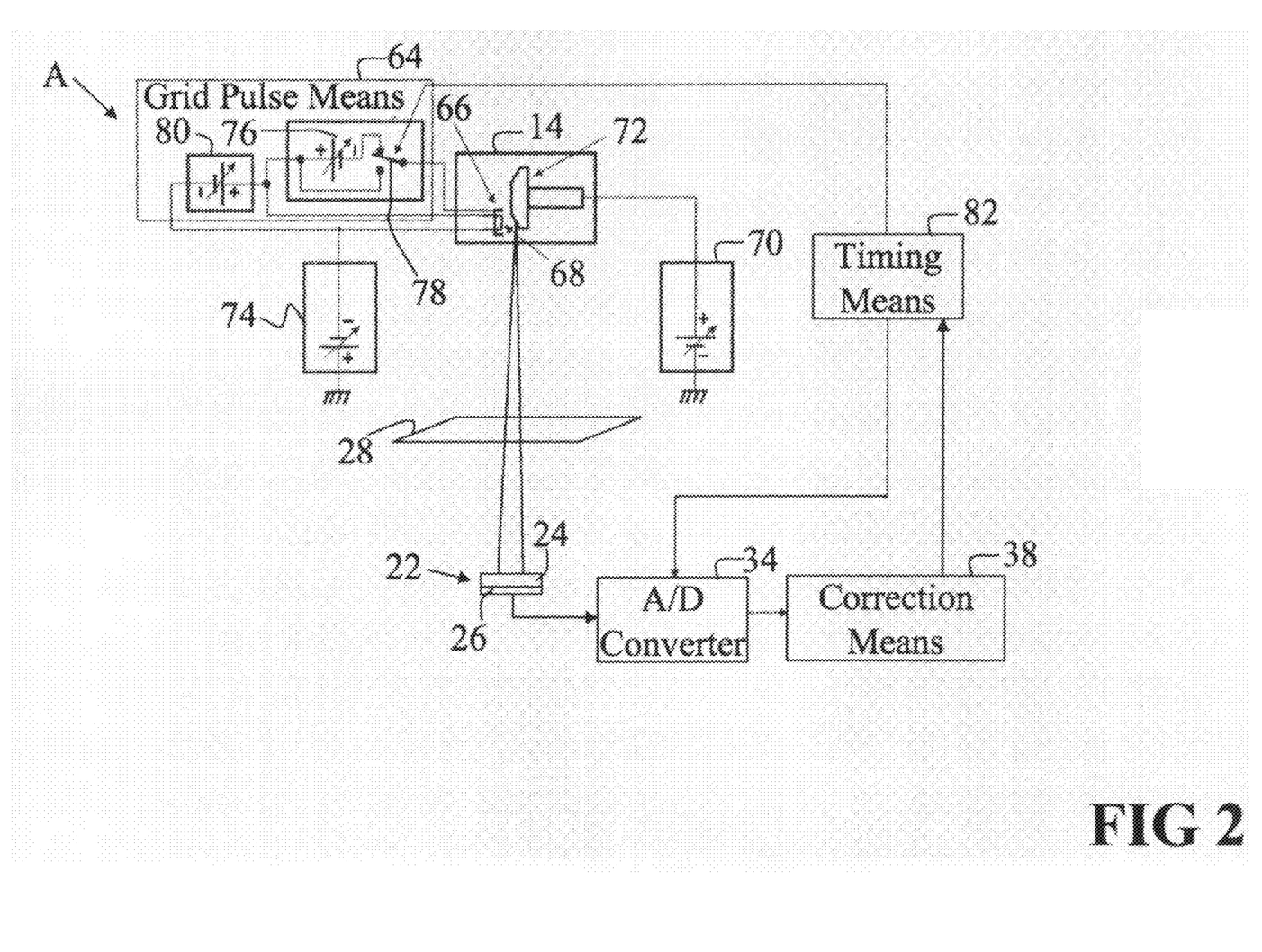
FIG. 2 shows a diagrammatic representation of a portion of an imaging system which includes a pulsed x-ray source.

With continuing reference to FIG. 1 and further reference to FIG. 2, a grid pulse circuit or means 64 turns the x-ray tube 14 ON and OFF at a rate of about 1000 to 5000 pulses per second to allow a time varying offset B(t) to be measured the same number of times per second, i.e., continuously over time. At a sampling rate of 1000-5000 pulses per second, the offset B(t) only needs to be considered constant for a time on the order of 100's of microseconds. This assumption is quite reasonable for a wide range of the low grade scintillators and x-ray photoconductors that might be used with to manufacture the detector 18. Preferably, a pulse rise time $T_r$ and a pulse fall time $T_f$ is equal to or less than 1 usec.

More specifically, the fast switching is achieved by quickly switching the potential on a cathode cup or grid 66 relative to a filament 68. Turning to a circuit A, a positive high voltage power supply 70 is connected to an anode 72 of the x-ray tube 14. A negative high voltage power supply 74 is connected to the cathode 66 of the x-ray tube 14. A voltage for each of the power supplies 70, 74 is preferably about +60,000 volts/−60,000 volts, respectively, which results in a total potential from the anode 72 to the cathode 66 of 120,000 volts. The grid pulse means 64 includes a grid power supply 76, a switch 78 and a filament power supply 80 which supply a pulse potential to the grid 66 and the filament 68. The grid pulse voltage is preferably from 1000 to 5000 volts. As the switch 78 receives command signals from a timing control unit or means 82 to close or open, the grid pulse means 64 changes the potential on the cathode 66 relative to the potential on the filament 68. When the voltage on the cathode 66 is made negative relative to the filament by approximately a few thousand volts, the electron beam becomes pinched off and the x-rays are distinguished. The correction means 38 measures the signal, calculates correction and applies it to the measurement.

Figure 3A:
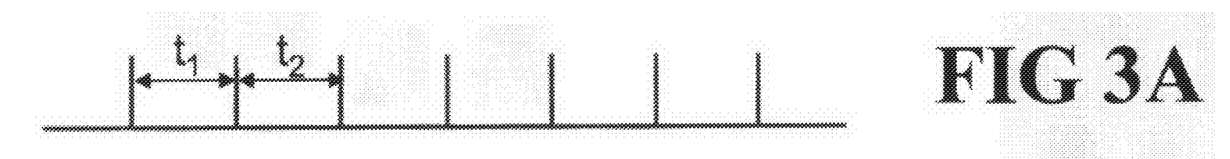
FIG. 3A shows a timing diagram of data collection.
Figure 3B:
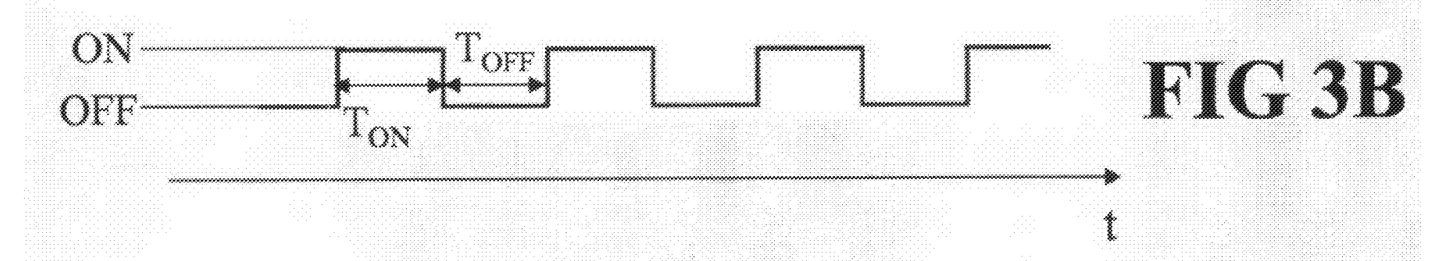
FIG. 3B shows a timing diagram of pulsing x-ray source.

With continuing reference to FIGS. 1 and 2 and further reference to FIGS. 3A and 3B, during an ON time $t_1$ of the x-ray source 14, the measured signal $S(t_1)$ is generally equal to:

$$S(t_1)=A(t_1)\cdot X(t_1)+B(t_1), \text{ where}$$

$S(t_1)$ is a measured signal of the detector 18 during the x-ray source ON time $t_1$,
$X(t_1)$ is an incident x-ray intensity on the detector 18,
$A(t_1)$ is a gain of the detector 18 during the ON time $t_1$, and
$B(t_1)$ is a signal offset of the detector 18 during the ON time $t_1$.

During a time $t_2$, the x-ray source 14 is OFF, an offset measuring means 84 measures the offset $B(t_2)$ which is equal to the measured signal $S(t_2)$:

$$S(t_2)=B(t_2), \text{ where}$$

$S(t_2)$ is a measured signal of the detector 18 during the OFF time $t_2$, and
$B(t_2)$ is a measured offset of the detector 18 during the OFF time $t_2$.

Because the ON time $t_1$ and the OFF time $t_2$ are close in time to each other, e.g. within 200 usec, the change in offset is only minor and can be neglected. E.g., the value of the measured offset $B(t_2)$ is nearly equal to the value of the signal offset $B(t_1)$:

$$B(t_2) \approx B(t_1)$$

The correction means 38 calculates a corrected signal value by subtracting the measured offset $B(t_2)$ from the measured signal $S(t_1)$ to obtain the corrected signal $S_C(t_1)$:

$$S_C(t_1)=[A(t_1)\cdot X(t_1)+B(t_1)]-B(t_2) \approx A(t_1)\cdot X(t_1)$$

or $$S_C(t_1)=S(t_1)-S(t_2), \text{ where}$$

$S_C(t_1)$ is a corrected signal value,
$X(t_1)$ is an incident x-ray intensity on the detector 18,
$A(t_1)$ is a gain of the detector 18 during the ON time $t_1$,
$B(t_1)$ is a signal offset of the detector 18 during the ON time $t_1$,
$B(t_2)$ is a measured offset of the detector 18 during the OFF time $t_2$,
$S(t_1)$ is a measured signal of the detector 18 during the ON time $t_1$, and
$S(t_2)$ is a measured signal of the detector 18 during the OFF time $t_2$.

In timing diagrams of FIGS. 3A and 3B, the ON time $T_{ON}$ and the OFF time $T_{OFF}$ for the x-ray pulse is shown to be the same width as the data collection intervals. Of course, it is also contemplated that at least one of the ON time $T_{ON}$ and OFF time $T_{OFF}$ for the x-ray pulse can be shorter than the data collection interval, for example, to allow time for the detector signal to decay before an offset measurement is taken. Alternatively, the ON and OFF times of the x-ray source might be of different lengths of time. The respective data collection intervals for the ON and OFF times of the radiation source might vary in lengths as appropriate.

Figure 4:
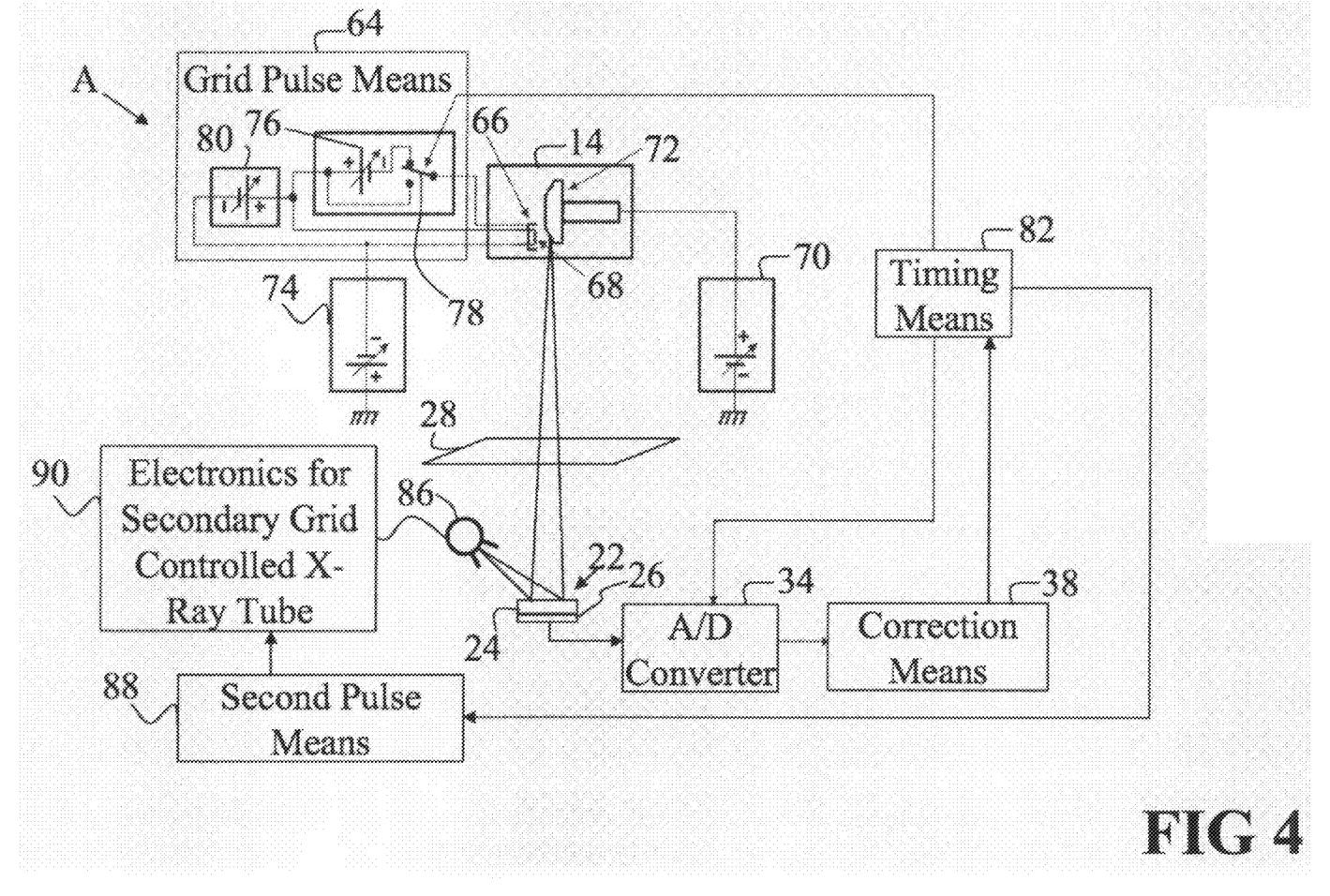
FIG. 4 diagrammatically shows a portion of the CT system with a pulsed primary x-ray source and a pulsed secondary x-ray source.

With continuing reference to FIG. 1 and further reference to FIG. 4, a secondary illumination source 86 such as an x-ray source, is added to the circuit A of FIG. 2 to continuously measure the gain A(t) of the detector 18 with the same timing as the offset measurements. A measurement of the gain can be done by turning OFF the primary x-ray source 14 and turning ON the secondary x-ray source 86 that illuminates the detectors directly rather than through the subject. The illumination source 86 produces the secondary illumination of a constant intensity $X_{Ref}$ which is used as the reference illumination to measure the detector gain A(t). Preferably, the secondary x-ray source 86 is an x-ray source of a lower radiation intensity than the primary x-ray source 14. The secondary source 86 is preferably disposed in a closer proximity to the detector 18 than the primary x-ray source 14 such that the illumination from the secondary source 86 does not pass through the subject 28. In one embodiment, for example, the primary x-ray tube 14 is rated between 100 and 500 mA, while the secondary x-ray source 86 can be rated between 1 and 2 mA. Such secondary x-ray source 86 has a small footprint and is cost effective. One possible position to dispose the secondary x-ray source 86 is behind the detector 18 such that the x-rays pass through the back of the detector 18. The secondary x-ray source 86 might be a field emission x-ray tube or fast shuttered radioisotope source.

The secondary source 86 is a grid controlled x-ray tube, similar to the primary x-ray tube 14. A secondary pulse means 88 turns the secondary x-ray source 86 ON and OFF at a rate of about 1000 to 5000 pulses per second. Preferably, a pulse rise time T'$_r$ and a pulse fall time T'$_f$ are equal to or less than 1 usec. An appropriate electronics 90 is included with the circuitry. The electronics 90 preferably includes a positive high voltage power supply to supply a high power to an anode of the secondary x-ray source 86, a negative high voltage power supply to supply a negative high power to a grid of the x-ray source 86, a grid power supply, a switch and a filament power supply to supply a pulse potential to the grid and a filament of the secondary x-ray source 86. The secondary pulse means 88 receives command signals from the timing control unit or means 82 to close or open the switch of the secondary pulse means to change the potential to the grid relative to the filament to quickly extinguish x-rays.

Figure 5A:
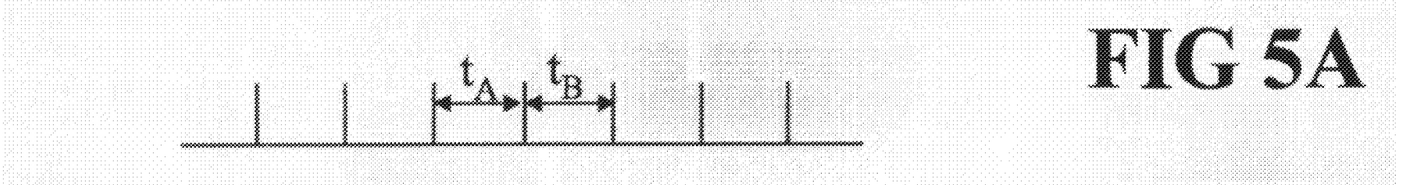
FIG. 5A shows a timing diagram of a data collection for a gain calibration.
Figure 5B:
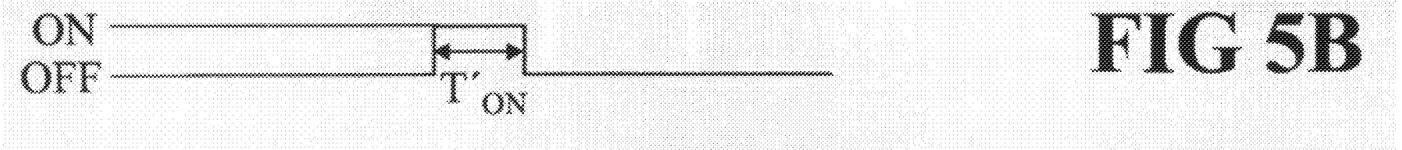
FIG. 5B shows a timing diagram of pulsing the secondary source during a gain calibration.

With continuing reference to FIGS. 1 and 4 and further reference to FIGS. 5A and 5B, sometime prior to scanning, a calibration process or means 92 measures a nominal or calibration gain $A_{cal}$ of the detector 18. The future measurements are corrected to the nominal gain. The calibration process 92 includes two measurements that are made in quick succession. The first measurement $S(t_A)$ is taken when the secondary x-ray source 86 is ON during a time $t_A$. The second measurement $S(t_B)$ is taken when the secondary x-ray source 86 is OFF at a time $t_B$. The two measured signals $S(t_A)$, $S(t_B)$ have the relations:

$$S(t_A) = A_{Cal} \cdot X_{Ref} + B(t_A) \quad (1)$$

$S(t_B) = B(t_B)$, where $S(t_A)$ is a measured signal of the detector during the time $t_A$,
$X_{REF}$ is an intensity of the secondary source 86,
$A_{Cal}$ is a calibration gain of detector 18 during the time $t_A$,
$B(t_A)$ is a signal offset of the detector 18 during the time $t_A$,
$S(t_B)$ is a measured signal of the detector 18 during the time $t_B$, and
$B(t_B)$ is a measured offset of the detector 18 during the time $t_B$.

Because times $t_A$ and $t_B$ are close in time, the change in offset is only minor and can be neglected. Therefore, the measured offset $B(t_B)$ is approximately equal to the signal offset $B(t_A)$. The value of the calibration gain $A_{Cal}$ is equal to:

$$A_{Cal} = [S(t_A) - B(t_A)]/X_{Ref} \text{ or}$$

$$A_{Cal} = [S(t_A) - S(t_B)]/X_{Ref}$$

$A_{Cal}$ is a calibration gain of detector 18 during the time $t_A$,
$S(t_A)$ is a measured signal of the detector during the time $t_A$,
$B(t_A)$ is a signal offset of the detector 18 during the time $t_A$,
$X_{REF}$ is an intensity of the secondary source 86, and
$S(t_B)$ is a measured signal of the detector 18 during the time $t_B$.

Figure 5C:
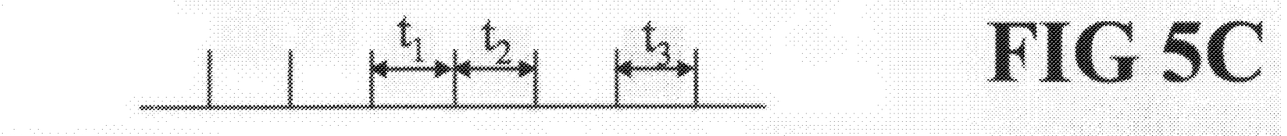
FIG. 5C shows a timing diagram of data collection during scan for the imaging system which includes two pulsed sources.
Figure 5D:
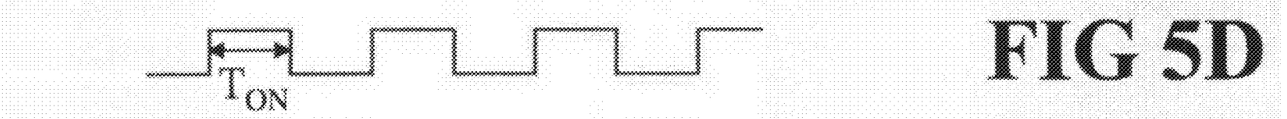
FIG. 5D shows a timing diagram of pulsing a primary x-ray source during scan.
Figure 5E:
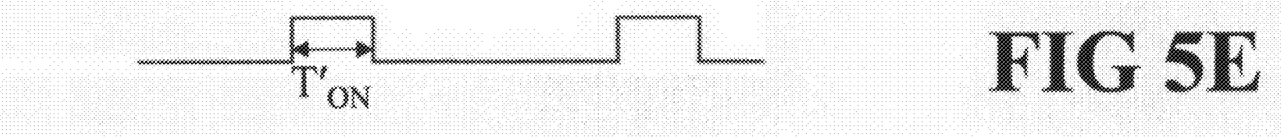
FIG. 5E shows a timing diagram of pulsing a secondary source during scan.

With continuing reference to FIGS. 1 and 4 and further reference to FIGS. 5C-5E, a gain measuring means 94 calculates the gain of the detector 18. Initially, the secondary x-ray source 86 is OFF. During the time $t_1$, the primary x-ray source 14 is ON. The measured signal $S(t_1)$ during the time $t_1$ is equal to:

$$S(t_1) = A(t_1) \cdot X(t_1) + B(t_1), \text{ where}$$

$S(t_1)$ is a measured signal of the detector 18 during the time $t_1$,
$X(t_1)$ is an incident x-ray intensity on the detector 18,
$A(t_1)$ is a gain of the detector 18 during the time $t_1$, and
$B(t_1)$ is a signal offset of the detector 18 during the time $t_1$.

As explained above, during the OFF time $t_2$, the offset measuring means 84 measures the offset $B(t_2)$, which is equal to the measured signal $S(t_2)$:

$$S(t_2) = B(t_2), \text{ where}$$

$S(t_2)$ is a measured signal of the detector 18 during the OFF time $t_2$, and
$B(t_2)$ is a measured offset of the detector 18 during the OFF time $t_2$.

During a time $t_3$, which is close in time to the times $t_1$ and $t_2$, the gain measuring means 94 measures the gain of the detector 18. More specifically, the timing means 82 sends a command to turn OFF the x-ray source 14 and turn ON the secondary x-ray source 86. The measured signal $S(t_3)$ during the time $t_3$ is equal to:

$$S(t_3) = A(t_3) \cdot X_{Ref} + B(t_3), \text{ where}$$

$S(t_3)$ is a measured signal of the detector 18 during the time $t_3$,
$A(t_3)$ is a signal gain of the detector 18 during the time $t_3$,
$X_{REF}$ is an intensity of the secondary source 86, and
$B(t_3)$ is a signal offset of the detector 18 during the time $t_3$.

The corrected signal $S_C(t_1)$, which is a close approximation to the desired signal is equal to:

$$S_C(t_1) = A_{Cal} \cdot X(t_1), \text{ where}$$

$S_C(t_1)$ is a corrected signal of the detector during the time $t_1$,
$X(t_1)$ is an incident x-ray intensity on the detector 18, and
$A_{Cal}$ is a calibration gain of detector 18.

If the calibration gain $A_{cal}$ is equal to $[S(t_A) - S(t_B)]/X_{Ref}$ and the x-ray intensity $X(t_1)$ is equal to $[S(t_1) - B(t_1)]/A(t_1)$, then the corrected signal $S_C(t_1)$ is equal to:

$$S_C(t_1) = \{[S(t_A) - S(t_B)]/X_{Ref}\} \cdot \{[S(t_1) - B(t_1)]/A(t_1)\},$$
where $S_C(t_1)$ is a corrected signal of the detector 18 during the time $t_1$,
$S(t_A)$ is a measured signal of the detector 18 during the time $t_A$,
$S(t_B)$ is a measured signal of the detector 18 during the time $t_B$,
$X_{REF}$ is an intensity of the secondary source 86,
$S(t_1)$ is a measured signal of the detector 18 during the time $t_1$,
$B(t_1)$ is a signal offset of the detector 18 during the time $t_1$, and
$A(t_1)$ is a signal gain of the detector 18 during the time $t_1$.

An assumption here is made that the times $t_1$, $t_2$ and $t_3$ are close in time; e.g. the detector offset stays constant at the times $t_1$, $t_2$, $t_3$, therefore, $B(t_1) \approx B(t_2) = S(t_2)$, thus the corrected signal $S_C(t_1)$ is equal to:

$$S_C(t_1) = \{[S(t_A) - S(t_B)]/X_{Ref}\} \cdot \{[S(t_1) - S(t_2)]/A(t_1)\}$$

Since $A(t_1) \approx A(t_3) = \{[S(t_3) - B(t_3)]/X\text{Ref}\}$ and $B(t_3) \approx B(t_2) = S(t_2)$, then:

$$S_C(t_1) = \{[S(t_A) - S(t_B)] \cdot [S(t_1) - S(t_2)]\}/\{S(t_3) - S(t_2)\},$$
where $S_C(t_1)$ is a corrected signal of the detector 18 during the time $t_1$,
$S(t_A)$ is a measured signal of the detector 18 during the time $t_A$,
$S(t_B)$ is a measured signal of the detector 18 during the time $t_B$,
$S(t_1)$ is a measured signal of the detector 18 during the time $t_1$,
$S(t_2)$ is a measured signal of the detector 18 during the time $t_2$,
$S(t_3)$ is a measured signal of the detector 18 during the time $t_3$.

Therefore, the correction means 38 corrects the gain and offset of the signal $S(t_1)$ at the time $t_1$ to yield the corrected signal $S_C(t_1)$ which is the corrected signal at the time $t_1$. The corrected signal $S_C(t_1)$ is a close approximation of the measured signal $S'(t_1)$ would occur if the gain $A(t)$ were a constant value of $A_{Ref}$ and the offset was equal to zero.

In one embodiment, to reduce noise it is also possible to smooth or average the offset and gain measurements over time.

As shown in FIGS. 5C, 5D and 5E, in a timing diagram for the system which includes two pulsed x-ray sources for continuous gain $A(t)$ and offset $B(t)$ correction, the ON time $T_{ON}$ and the OFF time $T_{OFF}$ for the x-ray pulse of the x-ray source 14 is shown to be the same width as the data collection intervals. Of course, it is also contemplated that at least one of the ON time $T_{ON}$ and OFF time Toss for the x-ray pulse of the x-ray source 14 can be shorter than the data collection interval, for example, to allow time for the detector signal to decay before an offset measurement is taken. Alternatively, the ON and OFF times of the x-ray source might be of different lengths of time. The respective data collection intervals for the ON and OFF times of the x-ray source might vary in lengths as appropriate.

Figure 6A:
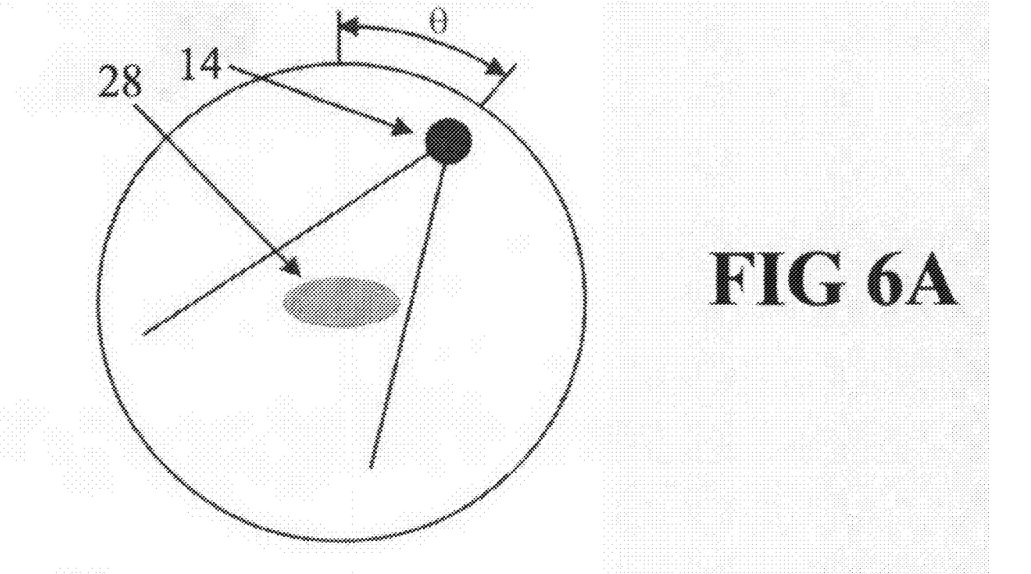
FIG. 6A diagrammatically shows a field of view of a detector.
Figure 6B:
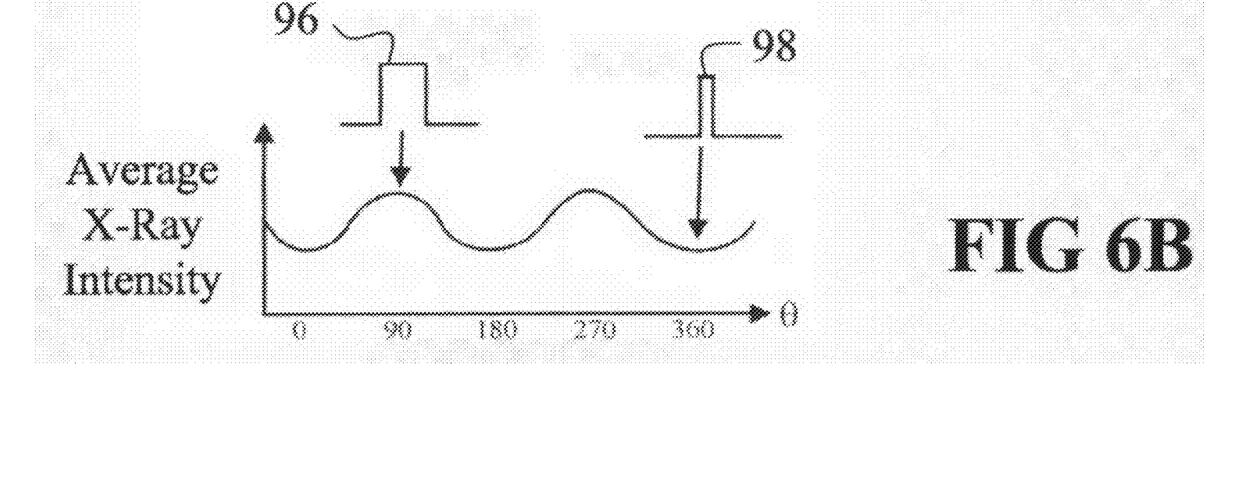
FIG. 6B shows a graph of average x-ray intensity which is modulated by a fast pulsing of an x-ray source.

With reference to FIGS. 6A and 6B, the x-ray tube 14 intensity is varied continuously to achieve a fast dose modulation and reduce the overall radiation dose delivered to the patient. In the CT scanners, it is common to vary the current to the filament 68 of the x-ray tube 14 in order to vary the x-ray intensity during a scan. More x-rays are typically required when the x-rays must pass through the thick anatomy of the subject 28; while fewer x-rays are used when the imaging is done in the regions with a thin anatomy. When the average x-ray intensity is required to be large, e.g it is known that the x-rays have to go through a wide part of the subject 28, the long x-ray pulses 96 are used. When less average intensity is required, e.g it is known that the x-rays have to go through a thinner part of the subject 28, the shorter pulses 98 are used. By reducing the x-ray intensity when the x-rays pass through thin sections of the patient anatomy, the overall patient's dose is reduced The average x-ray intensity stays nearly constant over scan.

Figure 7:
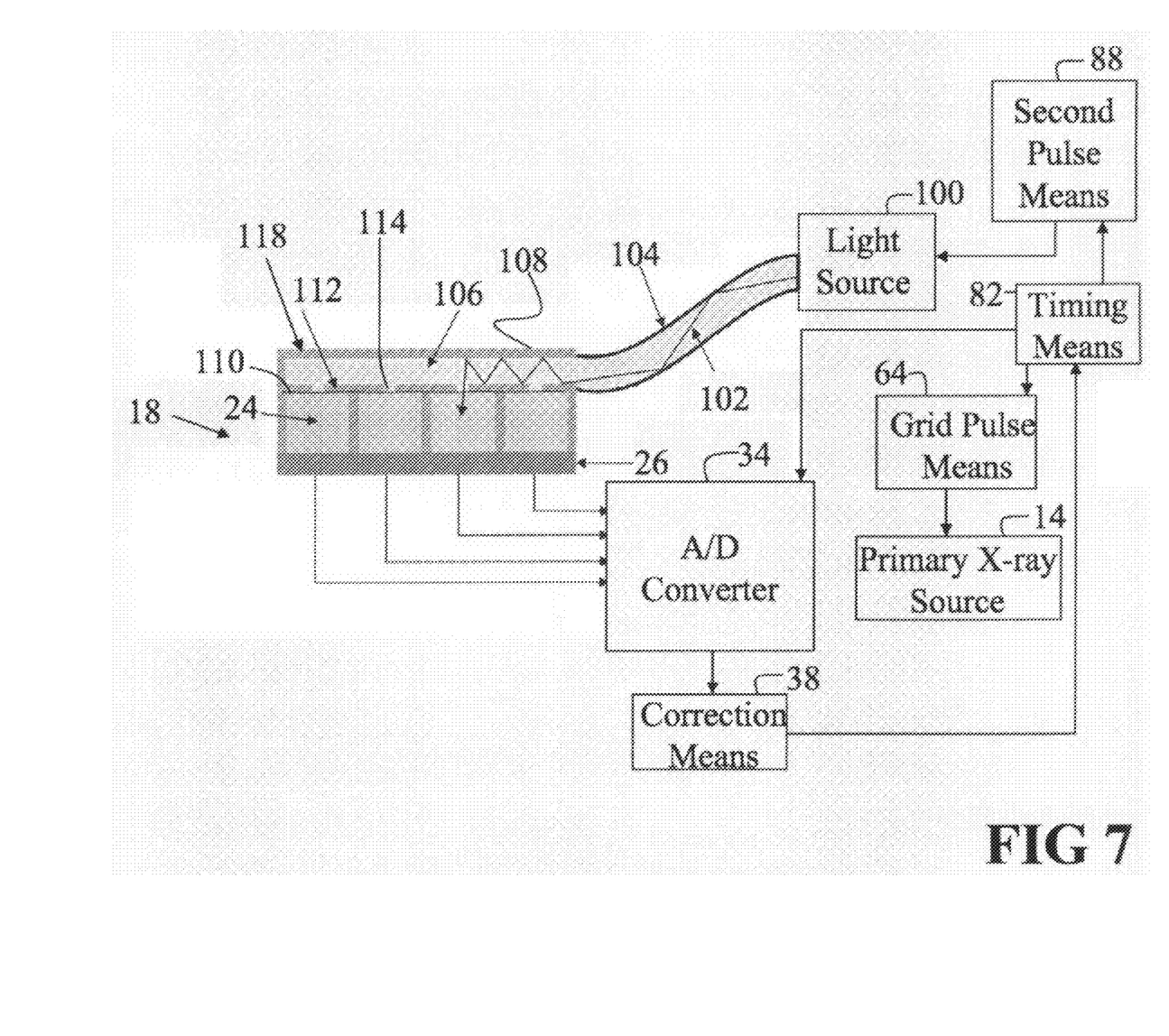
FIG. 7 diagrammatically shows a detailed portion of the CT imaging system in which the secondary pulsed source is a light source.

With reference to FIG. 7, a pulsed light source 100 such as an ultraviolet light (UV) is used to excite the scintillator 24 to introduce light into the detector 18 that is detected by the photodiodes 26. The light injected into the scintillating layer 24 is absorbed similar to the x-rays which are absorbed in the same material. An ultraviolet light 102 is guided by a fiber optic 104 and a light guide 106 into the detector 18. The photodiodes 26 are substantially insensitive to the UV light. Preferably, the photodiodes 26 are inherently UV blind. Alternatively, a UV blocking filter layer can be deposited on the photodiode surface. The ultraviolet light 102 is used as a reference illumination in place of the secondary x-ray source of FIG. 4 for measuring the detector gain A(t). More specifically, a UV light pipe 108 is mounted to an inner surface 110 of the scintillating layer 24. The inner surface 110 is preferably painted with a reflective layer 112. Small openings 114 in the reflective layer allow the UV light 102 to reach the scintillating layer 24 such that the light 102 spreads out to illuminate the scintillating crystals and reach the photodiodes 26 which produce electrical signals in proportion to the light. The signals are measured and corrected by the correction means 38 as it is explained above.

The UV light pipe 108 is substantially transparent to x-rays and could be made from any UV transparent material such as certain glasses, quartz, and the like. The light pipe 108 preferably is coated with a second layer 118 of a reflective material to keep the UV light 102 from escaping the pipe 108. The UV intensity reaching each detector element need not be equal since a correction for unequal intensities can be made. In one embodiment, a single UV source 100 serves several detection modules using multiple fiber optics.

Figure 8:
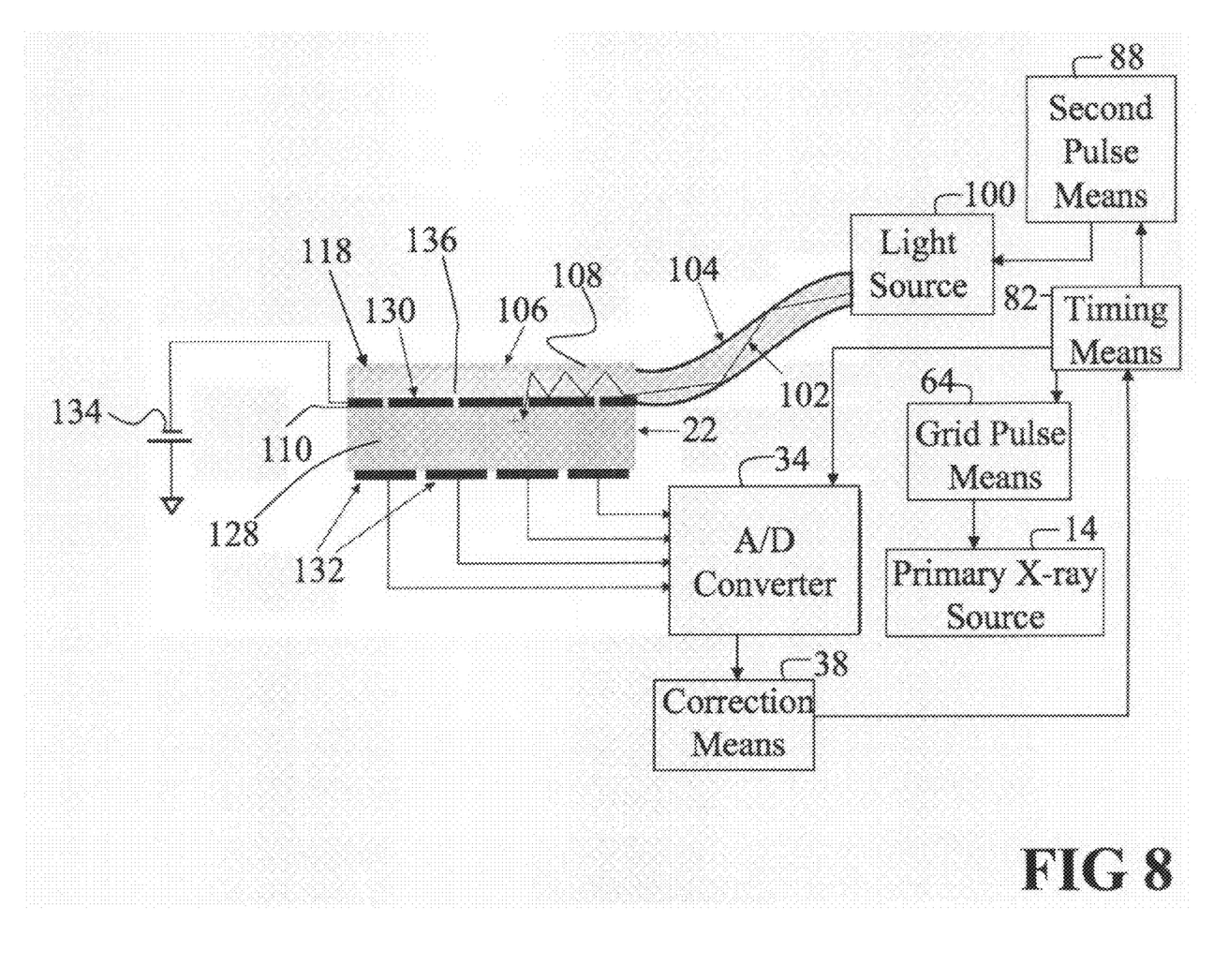
FIG. 8 diagrammatically shows a detailed portion of the CT imaging system in which the detector includes an x-ray photoconductor and the secondary pulsed source is a light source.

With reference to FIG. 8, the x-ray to analog converting layer 22 includes an x-ray photoconductor 128 which is excited by the pulsed light source 100. The light injected into the photoconductor 128 produces carriers which are similar to the carriers produced by the x-rays which are absorbed in the same material. The light source 100 produces the reference illumination used for the detector gain measurement. The x-ray photoconductor 128 includes a top electrode layer 130 and bottom or pixel electrodes 132. A high voltage power supply 134 supplies a high voltage bias to the detector 18 via the top electrode 130. The light pipe 108 is disposed above the top electrode 130 to distribute the light 102 to the openings 136 in the top electrode layer 130 via the fiber optic 104 and the light guide 106. The light pipe 108 is preferably substantially transparent to x-rays and could be made of optically clear glass, plastic or other like transparent materials. The bottom electrodes 132 are individual electrodes that detect the signals for several separate x-ray sensitive regions of the detector 18. The signals are measured and corrected by the correction means 38 as it is explained above.

Figure 9:
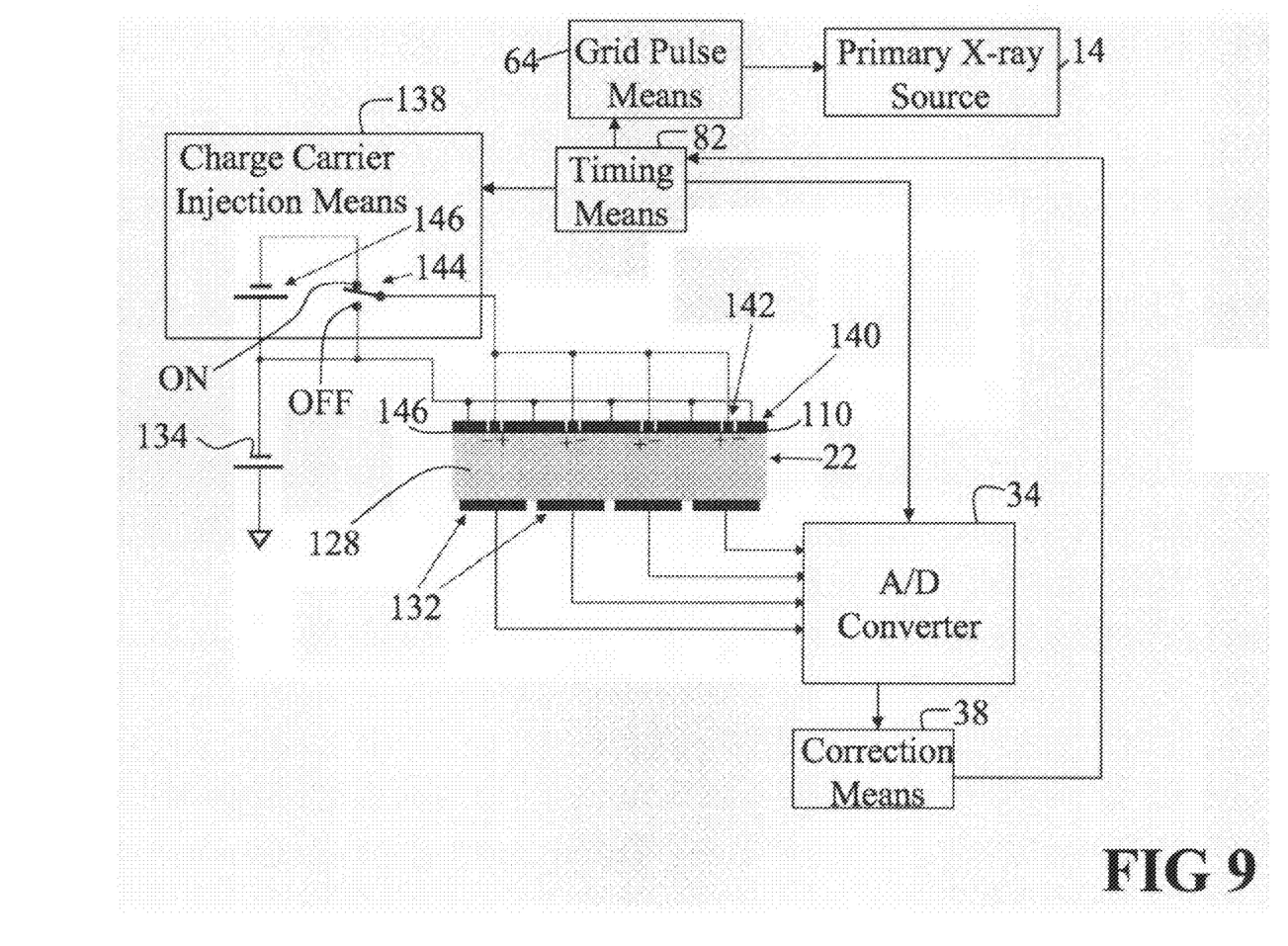
FIG. 9 diagrammatically shows a detailed portion of the CT imaging system in which the detector includes an x-ray photoconductor and the secondary pulsed source is a charge carrier injection source.

With reference to FIG. 9, a charge carrier injecting means 138 injects carriers into the photoconductor 128. Such artificially injected carriers behave in substantially the same manner as the carriers created by the x-rays. Trapping effects in the photoconductor, which affect the gain during x-ray detection, also affect the gain for carrier injection by electrodes. More specifically, for the purpose of measuring the detector gain A(t), the top electrode layer 130 is partitioned into two or more electrodes, e.g. a common bias and injection top electrodes 140, 142. Under regular scanning conditions, the top electrodes 140, 142 are at the same fixed potential. More specifically, when a switch 144 is in an "OFF" position, the high voltage power supply 134 supplies the high voltage bias to both top electrodes 140, 142. During the measurement of the detector gain A(t), the primary x-ray source 14 is turned OFF. The switch 144 is in an "ON" position. An injection power supply 146 supplies an injection potential to the injection electrodes 142 while the high voltage power supply 134 supplies the high voltage bias to the common bias electrodes 140. In this manner, a differential voltage is applied to the common bias and injection electrodes 140, 142. The differential voltage causes injection of carriers into the photoconductor 128 at the top surface 110. The carriers create a signal which is detected by the bottom electrodes 132. The signal is measured and corrected by the correction means 38 as it is explained above.

To prevent unwanted carriers from being injected into the photoconductor 128, a thin layer 146, also called a blocking contact, is disposed between the metal top electrodes 140, 142 and the x-ray photoconductor 128. Injection of the unwanted carriers results in high dark current which is a highly undesirable effect. The blocking contact 146 can be formed by different methods such as P-N junction, a Schottky barrier, an insulating -tunneling barrier, and the like. Under normal conditions, when the high voltage bias is applied, the blocking contact 146 prevents injection of the carriers. The application of an extra high differential potential to the top electrodes 140, 142 causes a non-destructive breakdown of the blocking contact 146 with a resulting injection of carriers. Each of the three types of blocking contacts mentioned above is prone to this breakdown.

The use of a pulsed x-ray source in combination with the above described mathematical correction will allow detectors to be used for which gain and offset vary with time. The examples of such previously unusable detectors are detectors made of low grade scintillators, x-ray photoconductors, and the like.

In one embodiment, a statistical history of changes in the detector's offset and/or gain with time is collected. The system is calibrated less frequently based on the collected history.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A radiographic imaging apparatus comprising:
   a primary radiation source which projects a beam of radiation into an examination region in which a subject is disposed for an examination, the primary radiation source having an ON state and an OFF state;
   a detector which converts detected radiation passing through the examination region into electrical detector signals representative of the detected radiation and a temporally changing offset B(t);
   an offset measuring circuit which measures a value ($B_2$) of the offset when the primary source is in the OFF state;
   a grid pulse circuit which turns the primary radiation source between the ON and OFF states at a rate between 1000 and 5000 pulses per second, such that the offset B(t) is re-measured between 1000 and 5000 times per second;
   a correction circuit which determines corrections to the detector signals to compensate for the temporally changing offset B(t) from the measured offset values and corrects the detector signals with the determined corrections.

2. A Computed Tomography (CT) scanner including:
a gantry mounted to rotate around an examination region;
an x-ray source mounted to the gantry to irradiate the examination region with a beam of x-rays during rotation around the examination region;
a pulsing circuit which pulses the x-ray source ON and OFF at least 1000 times per second as the x-ray source rotates around the examination region;
an x-ray detector which receives x-rays from the x-ray source that have traversed the examination region, the x-ray detector outputting detector signals indicative of (1) x-rays passing through the examination region and a temporally varying detector offset when the x-ray source is ON and (2) the temporally varying offset when the x-ray source is OFF;
an offset correction component which corrects the detector signals output when the x-ray source is ON with the detector signals output when the x-ray source is OFF to correct for the temporally varying offset;
a second radiation source of a constant intensity (XRef) for exciting the detector;
a second pulsing circuit which pulses the second source during a time that the x-ray source is OFF; and
a gain calibration unit which determines a normal gain ($A_{Cal}$) of the detector at least 1000 times per second from a strength of a signal ($S_A$) measured when the second source is ON during a time ($t_A$) and a signal ($S_B$) measured during a time ($t_B$) when the second source and the x-ray source are OFF.

3. The CT scanner as set forth in claim 2, wherein the gain calibration unit calculates:

$$A_{Cal}=[S_A-S_B]/X_{Ref}$$

$A_{Cal}$ is the calibration gain of the detector,
$S_A$ is the measured signal of the detector during the time ($t_A$),
$X_{Ref}$ is the intensity of the secondary source, and
$S_B$ is the measured signal of the detector during the time ($t_B$).

4. The CT scanner as set forth in claim 3, further including a gaincorrection unit which corrects the signals output by the detector in accordance with a change in a gain (A(t)) of the detector as:

$$S_{C1}=\{[S_A-S_B]\cdot[S_1-S_2]\}/\{S_3-S_2\}, \text{ where}$$

$S_{C1}$ is a corrected signal of the detector during the time ($t_1$),
$S_A$ is the measured signal of the detector during the time ($t_A$),
$S_B$ is the measured signal of the detector during the time ($t_B$),
$S_1$ is the measured signal of the detector during the time ($t_1$),
$S_2$ is the measured signal of the detector during the time ($t_2$),
$S_3$ is a measured signal of the detector during a time ($t_3$),
wherein the time ($t_3$) is an ON time of the second source while the primary source is OFF, which time ($t_3$) is close in time to the times ($t_1$) and ($t_2$).

5. The CT scanner as set forth in claim 2, wherein the second radiation source is one of a second x-ray source, a light source and a carrier injecting source.

6. The CT scanner as set forth in claim 2, wherein the second radiation source is a UV light source.

7. A method of radiographic imaging comprising:
controlling projecting of a beam of radiation into an examination region in which a subject is disposed for an examination;
converting detected radiation passing through the examination region into electrical detector signals representative of the detected radiation and at least one temporally changing characteristic, the changing characteristic being an offset B(t);
determining a correction to the detector signals to compensate for the at least one temporally changing characteristic at a rate of at least 1000 times per second during generation of the detector signals; and
correcting the detector signals with the determined corrections, the correction step including measuring the offset of the detector and further including:
pulsing the beam of radiation at least 1000 times per second, the offset B(t) staying substantially constant during a primary radiation beam ON time ($t_1$) and a primary radiation beam OFF time ($t_2$); and
measuring a value ($B_2$) of the offset during the primary radiation beam OFF times ($t_2$), which offset value ($B_2$) is equal to a signal value ($S_2$) during the radiation beam OFF time ($t_2$).

8. The method as set forth in claim 7, wherein the step of pulsing includes:
turning a primary radiation source ON and OFF at a rate between 1000 and 5000 pulses per second; and
measuring the offset between 1000 and 5000 times per second.

9. The method as set forth in claim 7, further including:
exciting the detector with a second pulsed source of a constant intensity.

10. The method as set forth in claim 9, wherein the correction step further includes:
determining a nominal gain ($A_{Cal}$) of the detector in relation to a strength of a signal ($S_A$) measured when the second source is ON during a time ($t_A$) and the signal ($S_B$) measured when the second source is OFF during a time ($t_B$):

$$A_{Cal}=[S(t_A)-S(t_B)]/X_{Ref}$$

$A_{Cal}$ is a calibration gain of detector,
$S_A$ is a measured signal of the detector during the time ($t_A$),
$X_{Ref}$ is an intensity of the secondary source, and
$S_B$ is a measured signal of the detector during the time ($t_B$).

11. The method as set forth in claim 10, wherein the correction step further includes:
correcting the detected signal in accordance with a change of a gain ($A_t$) of the detector as:

$$S_{C1}=\{[S_A-S_B]\cdot[S_1-S_2]\}/\{S_3-S_2\}, \text{ where}$$

$S_{C1}$ is a corrected signal of the detector during the time ($t_1$),
$S_A$ is the measured signal of the detector during the time ($t_A$),
$S_B$ is the measured signal of the detector during the time ($t_B$),
$S_1$ is a measured signal of the detector during the time ($t_1$),
$S_2$ is a measured signal of the detector during the time ($t_2$),
$S_3$ is a measured signal of the detector during a time ($t_3$),
wherein the time ($t_3$) is an ON time of the second source while the primary source is OFF, which time ($t_3$) is close in time to the times ($t_1$) and ($t_2$).

12. The method as set forth in claim 7, wherein the detecting step includes:

detecting radiation events and converting the detected radiation events into electrical signals with an array of x-ray photoconductors.

13. The method as set forth in claim 7, further including:
during at least some of the OFF times, exciting the detectors with one of lower energy x-ray radiation, light, and injected charge carriers.

14. A computed tomography scanner including a processor programmed to perform the method of claim 7.

15. A non-transient tangible computer-readable medium carrying a computer program for controlling one or more processors to perform the method of claim 7.

16. A method of radiographic imaging comprising:
controlling projecting of a beam of radiation into an examination region in which a subject is disposed for an examination;
converting detected radiation passing through the examination region into electrical detector signals representative of the detected radiation and at least one temporally changing characteristic, the changing characteristic including a gain A(t);
rotating the primary radiation source around an axial direction to project the radiation beam at a variety of angular positions;
exciting the detector with a second pulsed source of a constant intensity;
pulsing the primary source;
pulsing the second source when the primary source is OFF;
re-measuring and correcting the gain A(t) at a rate of pulsing of the second source;
determining a correction to the detector signals to compensate for the at least one temporally changing characteristic at a rate of at least 1000 times per second during generation of the detector signals; and
correcting the detector signals with the determined corrections.

17. The method as set forth in claim 16, further including:
continually adjusting an intensity of the primary source in accordance with an angular position of the primary source to achieve dose modulation.

18. A computed tomography scanner including a processor programmed to perform the method of claim 16.

19. A non-transient tangible computer-readable medium carrying a computer program for controlling one or more processors to perform the method of claim 16.

20. A Computed Tomography (CT) scanner including:
a gantry mounted to rotate around an examination region;
an x-ray source mounted to the gantry to irradiate the examination region with a beam of x-rays during rotation around the examination region;
a pulsing circuit which pulses the x-ray source ON and OFF a rate of at least 1000 times per second as the x-ray source rotates around the examination region;
an x-ray detector which receives x-rays from the x-ray source that have traversed the examination region, the radiation detector outputting detector signals indicative of (1) x-rays passing through the examination region and a temporally varying detector offset when the x-ray source is ON and (2) the temporally varying offset B(t) when the x-ray source is OFF, the offset B(t) staying substantially constant when the x-ray source is ON and when the x-ray source is OFF; and,
an offset correction component which (1) determines a correction to the detector signals to compensate for the temporally varying offset at a rate of at least 1000 times per second during generation of the detector signals including measuring a value ($B_2$) of the temporally varying offset when the x-ray source is OFF, the measured offset value ($B_2$) being equal to a signal value when the x-ray source is OFF corrects the detector signals output when the x-ray source is ON with the correction to correct for the temporally varying offset.

21. The CT scanner as set forth in claim 20, wherein the detector includes:
an array of scintillating crystals which crystals detect x-ray radiation events when the x-ray source is ON and convert the detected events into light which light continues at least until the x-ray source is next ON; and
an array of photodiodes which photodiodes are coupled to the scintillating crystals to detect light and convert the detected light into the detector signals.

22. The CT scanner as set forth in claim 21, wherein the correction circuit corrects the detected signal by subtracting the measured offset value ($B_2$) from the detected signal:

$$S_{C1} = A_1 X_1 - B_2, \text{ where}$$

$S_{C1}$ is the corrected signal during the time ($t_1$),
$A_1$ is a gain of the detector during the time ($t_1$),
$X_1$ is an incident x-ray intensity on the detector during the time ($t_1$), and
$B_2$ is the measured offset value of the detector during the time ($t_2$).

23. The CT scanner as set forth in claim 20, wherein the detector includes:
an array of x-ray photoconductors which photoconductors detect radiation events and convert the detected radiation events into the detector signals.

24. The CT scanner as set forth in claim 20, wherein the detector signals are analog and further including:
an A/D converter which converts the analog detector signals into a series of digital numbers and wherein the offset correction component is at least partially integrated with the A/D converter.

25. The CT scanner as set forth in claim 20, further including:
one of a light source and a carrier injecting source which is pulsed alternately with the x-ray source, the light or carrier injecting source being connected to the detector such that the light or injected carriers do not traverse the examination region.

* * * * *